(12) United States Patent
Drew et al.

(10) Patent No.: US 6,380,446 B1
(45) Date of Patent: Apr. 30, 2002

(54) PROCESS FOR DEHYDROHALOGENATION OF HALOGENATED COMPOUNDS

(75) Inventors: David William Drew, Newark, DE (US); Terry Wayne Redwine, Ponchatoula, LA (US)

(73) Assignee: DuPont Dow Elastomers, L.L.C., Wilmington, DE (US)

( * ) Notice: Subject to any disclaimer, the term of this patent is extended or adjusted under 35 U.S.C. 154(b) by 0 days.

(21) Appl. No.: 09/801,142

(22) Filed: Mar. 7, 2001

Related U.S. Application Data

(60) Provisional application No. 60/225,920, filed on Aug. 17, 2000.

(51) Int. Cl.[7] .............................................. C07C 17/25
(52) U.S. Cl. ........................ 570/228; 570/155; 570/156; 570/157
(58) Field of Search ................................ 570/157, 228, 570/156, 155

(56) References Cited

U.S. PATENT DOCUMENTS

| | | | |
|---|---|---|---|
| 3,639,493 A | 2/1972 | Campbell | |
| 3,772,461 A | 11/1973 | Horaguchi | |
| 3,876,716 A | 4/1975 | Campbell | |
| 3,981,937 A | 9/1976 | Campbell et al. | |
| 4,078,008 A | * 3/1978 | Lantzsch et al. | 570/228 |
| 4,104,316 A | 8/1978 | Scharfe et al. | |
| 4,418,232 A | 11/1983 | Maurin, III | |
| 5,107,040 A | * 4/1992 | Repman et al. | 570/228 |

OTHER PUBLICATIONS

Y. T. Shah, Et Al., Design Parameters Estimations for Bubble Column Reactors, American Institute of Chemical Engineers Journal (1982), pp. 353 through 379, vol. 28, No. 3.

Sheng–Yi Lee and Y. Pang Tsui, Succeed at Gas/Liquid Contacting, Chemical Engineering Progress (Jul. 1999), pp. 23 through 49.

* cited by examiner

*Primary Examiner*—Alan Siegel

(57) ABSTRACT

Halogenated compounds are dehydrohalogenated in a multi-stage bubble reactor wherein agitation of the reactor contents is provided by in situ generation and vaporization of reaction product having a boiling point lower than that of the reactants.

17 Claims, 1 Drawing Sheet

PROCESS FOR DEHYDROHALOGENATION OF HALOGENATED COMPOUNDS

CLAIM OF BENEFIT OF PRIOR APPLICATION

This application claims the benefit of U.S. Provisional Application No. 60/225,920 filed Aug. 17, 2000.

FIELD OF THE INVENTION

This invention relates to an improved process for production of alkenes from halogenated organic compounds. More specifically, this invention relates to a process for dehydrohalogenation of halogenated organic compounds using a staged upflow reactor.

BACKGROUND OF THE INVENTION

Dehydrohalogenation of halogenated organic compounds is generally conducted in the liquid phase by mixing a halogenated alkane or halogenated alkene with a strong base in a solvent. Because the base is usually added as an aqueous solution, phase transfer catalysts are often employed to promote contact of the reactants.

In many processes a series of continuous stirred tank reactors are used and by-products of the reaction, as well as unreacted starting materials, are removed by steam stripping or distillation. For example, 2-chloro-1,3-butadiene can be prepared by dehydrohalogenation of 3,4-dichlorobutene-1 in a series of co-current continuous stirred tank reactors using the catalytic process disclosed in U.S. Pat. No. 3,981,937. Other processes involve the use of boiling reactors, for example as disclosed in U.S. Pat. No. 3,772,461, or in stirred tanks coupled with phase decantation as disclosed in U.S. Pat. No. 4,418,232. Each of these methods is associated with disadvantages. The stirred reactor processes suffer from relatively low conversions and result in production of high levels of organic waste. Conversions in one-pass boiling reactor processes are typically extremely low, for example 85% or less. In addition, investment and energy costs associated with such processes are high.

Dehydrohalogenation processes that result in improved reactant conversion levels would result in production of lower levels of organic waste. These more efficient processes reduce production of halogenated organic compounds that can contribute to global warming. In addition, energy and material consumption are reduced.

SUMMARY OF THE INVENTION

The present invention is directed to an improved process for dehydrohalogenation of organic compounds. In particular, the present invention relates to a process for dehydrohalogenation of a halogenated compound selected from the group consisting of halogenated alkanes and halogenated alkenes, said process comprising A) contacting a first composition comprising said halogenated compound with a second composition comprising a base having a $K_b$ of at least $10^{-9}$, in the liquid phase, in a reactor having multiple stages, at a temperature sufficient to initiate the exothermic reaction of said halogenated compound with said base, thereby forming a dehydrohalogenated compound having a boiling point lower than that of said halogenated compound; and B) maintaining the temperature of the reactor contents at a temperature sufficient to vaporize said dehydrohalogenated compound thereby causing agitation of said reactor contents and transfer of vaporized dehydrohalogenated compound through said multiple stages of said reactor, said vaporization providing a means of agitation.

DETAILED DESCRIPTION OF THE INVENTION

Figure 1:
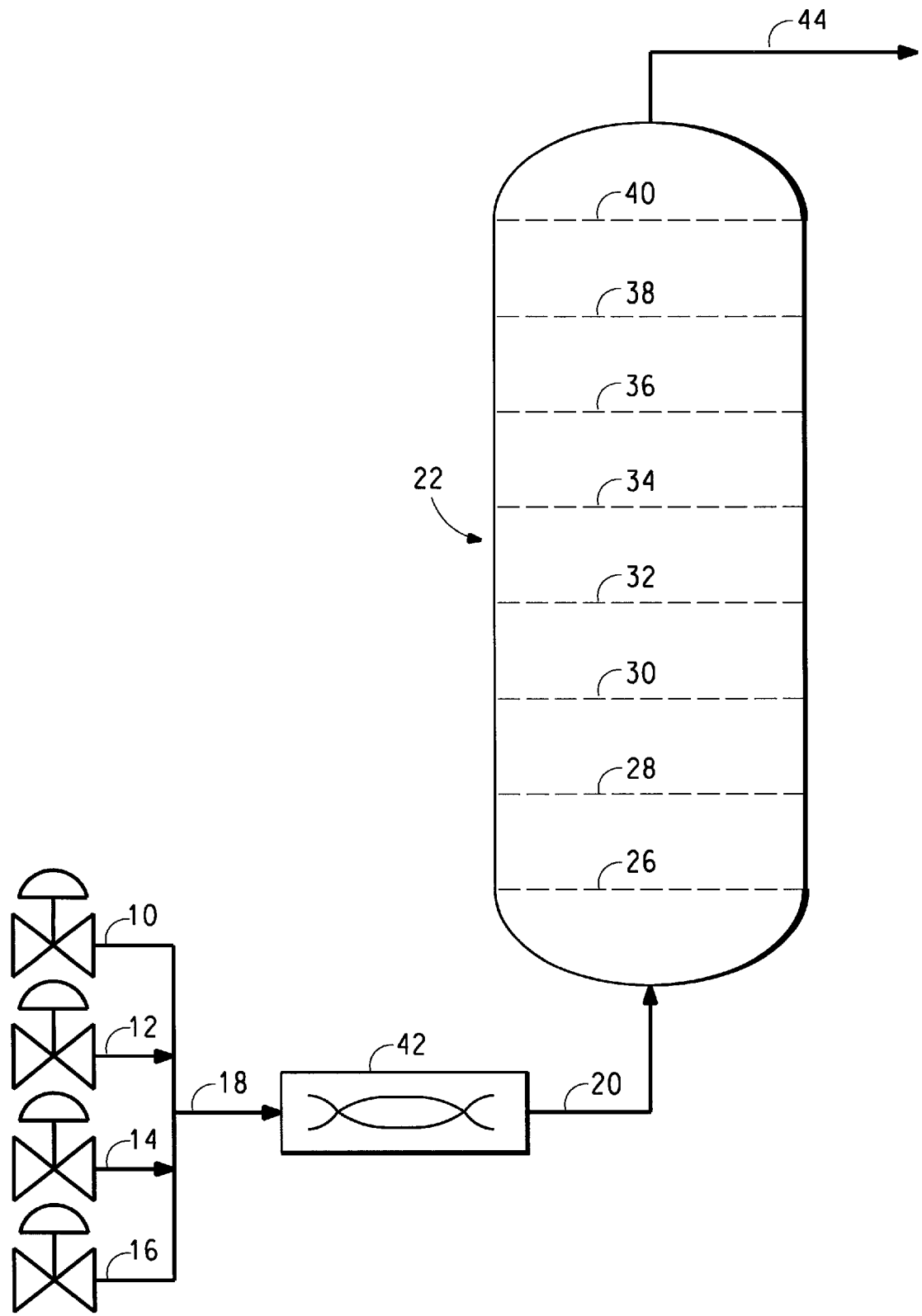
FIG. 1 is a schematic diagram of one embodiment of the process of the present invention.

The dehydrohalogenation process of the present invention takes place in the liquid phase in a staged bubble reactor. Bubble reactors are extensively used in the chemical industry and consist of a contact region in which a discontinuous gas phase in the form of bubbles moves relative to a continuous phase. Bubble reactors can be single staged or multistaged, single channel or multi-channel, batch or continuous. A preferred type of bubble reactor is a co-current vertical column containing multiple stages, hereinafter referred to as a multi-staged upflow reactor.

The halogenated organic compound or compounds that serve as the reactants may be selected from the group consisting of halogenated aliphatic alkanes or halogenated aliphatic alkenes. Preferred compounds are those having two to eight carbon atoms. Any saturated or unsaturated halogenated alkane or halogenated alkene that can be dehydrohalogenated with alkali is suitable for use in the process of the invention. These halogenated compounds will have at least one hydrogen atom. Fluorinated, chlorinated, brominated or iodinated alkanes or alkenes are all suitable reactants. Preferred halogenated compound reactants are chlorinated butadienes or chlorinated butenes. The halogenated alkanes or alkenes may contain a single species of halogen atom or they may contain more than one type of halogen atom. The process is particularly useful for dehydrochlorination of chlorinated alkanes and chlorinated alkenes in the presence of aqueous alkali. Examples of suitable halogenated alkanes or halogenated alkenes include 1,4-dichlorobutene-2; 3,4-dichlorobutene-1; 2,3,4-trichlorobutene-1; 2-chloro-3-bromobutene-1; 1,2-dibromopropane; 1,3-dichlorobutane; 1-iodo-2-chlorobutane; perfluorobutylethyliodide; and 1,4-dibromo-1,1,2,2-tetrafluorobutane.

The halogenated reactant may be in the form of a solid, a liquid or a gas at ambient temperature. However, liquid halogenated alkanes or alkenes are preferred. In addition, the halogenated reactant must either be a liquid or be present in a liquid phase under the conditions at which the dehydrohalogenation reaction is conducted.

The dehydrohalogenating agent, which is a base having a $K_b$ of at least $10^{-9}$, will generally be in the form of an aqueous solution, but it need not be. Suitable bases include pyridine, trimethylamine, ammonia, ammonium hydroxide, calcium hydroxide, alkali metal hydroxides, and alkali metal alkoxides. Preferably the base will have a $K_b$ of at least $10^{-5}$, and most preferably the base will be completely ionized, as in the case of aqueous alkali. Any aqueous alkali metal hydroxide is suitable for purposes of the invention, but sodium hydroxide and potassium hydroxide are preferred. The alkali normally will be present in excess in the reaction mixture. Generally, a mole ratio of alkali to halogenated reactant will be approximately 1.01–2.00. The precise amount will be determined based on factors such as the type of catalyst used and the particular reactants.

The reaction takes place in the liquid phase. The reaction mixture will normally contain at least one liquid. For example, the halogenated reactants may be liquids under conditions of the reaction or they may be dissolved in aqueous or non-aqueous solvents. If the reactants are present as solutions, the solvents may be miscible or immiscible. In a preferred embodiment the halogenated reactant is a liquid and an alkali metal hydroxide dehydrohalogenating agent is present as an aqueous solution. In addition, the dehydrohalogenation may take place in the presence of a non-aqueous solvent such as methanol, for example as disclosed in U.S. Pat. No. 4,104,316.

Preferably, especially in those cases where a halogenated liquid reactant is reacted with an aqueous solution of alkali metal hydroxide, a phase transfer catalyst is used to promote contact between the two immiscible liquids, i.e. the organic and aqueous phases. Preferred catalysts are quaternary ammonium salts, especially quaternary ammonium chlorides, particularly those represented by the formula $R^1R^2R^3R^4NCl$ in which each of $R^1$, $R^2$ and $R^3$ independently is a $C_1$–$C_{20}$ alky, a $C_2$–$C_{20}$ alkenyl, or a $C_7$–$C_{20}$ aralkyl, and $R_4$ is a $C_6$–$C_{20}$ alkyl or alkenyl, benzyl, or a ($C_6$–$C_{20}$) alkyl- or alkenyl-substituted benzyl. Each of $R^1$, $R^2$, and $R^3$ groups in these quaternary ammonium chlorides may also contain a hydroxyl or ether group in a position beta to the nitrogen atom. The amount of the quaternary ammonium compound is generally about 0.01–10% by weight of the starting halogenated alkane or alkene. Other phase transfer catalysts include amine oxides, such as those disclosed in U.S. Pat. No. 3,876,716 and quaternary phosphonium compounds, such as those disclosed in U.S. Pat. No. 3,639,493.

Other optional components may be present in the reaction mixture, for example inhibitors, stabilizers and dispersants. The use of such optional components will depend on the nature of the reactants and products to be produced.

In the process of the present invention, the halogenated alkane or halogenated alkene, and the base, are contacted in a bubble reactor in a liquid phase, thereby initiating an exothermic reaction to produce a dehydrohalogenated compound having a boiling point lower than that of the halogenated reactant. The heat liberated during the reaction vaporizes the dehydrohalogenated compound thus produced. It is to be understood that, if the halogenated alkane or alkene contains more than one site at which dehydrohalogenation can occur, then simultaneous dehydrohalogenation may take place. Thus, for example a halogenated alkane such as 1-chloro-4-bromobutane will lose hydrogen bromide and some hydrogen chloride when subjected to the conditions of the process of the present invention.

The vaporized product and water vapor that forms as a result of the dehydrohalogenation constitutes the gaseous phase that provides agitation of the reaction mixture as it moves through the reactor. Consequently, no internal stirring device is necessary within the reactor. Optionally, stirring means, such as a mechanical stirrer, can be present, but the presence of such devices is not necessary. Because the reaction is exothermic, it is not necessary to supply external heat to the reactor. In some instances it is useful to supply a small amount of heat initially for purposes of initiating the reaction or for temperature control.

The reactor is a multi-stage type, preferably having at least three stages, most preferably 4–20 stages. Reactors having only one stage provide low single pass conversion. Consequently, separation and recycle of the unconverted reactants must be undertaken which increases complexity and cost of the process when used on an industrial scale. Preferably the reactor will be a vertical column reactor because it greatly simplifies flow from stage to stage. That is, when an upflow reactor is employed, liquid reactants are entrained up through the stages by the rising bubbles. This eliminates the need for pumps to transfer reactants from stage to stage. In addition, the process of the present invention can take place in a series of continuous, distinct tanks or vessels.

In a preferred embodiment, chlorinated alkane or chlorinated alkene reactant and aqueous alkali metal hydroxide will be pre-mixed before introduction to the reactor. Examples of mixing devices include tanks fitted with mechanical agitators, that is stirred tank reactors, continuous stirred tank reactors, pumps and motionless stationary mixers. Reaction is initiated in the mixing device. This exothermic reaction provides heat and raises the vapor pressure to the point where some evaporation occurs upon entry to the bubble reactor. Mixing devices that are particularly useful in the practice of the invention include homogenizers, colloid mills, stirred tank reactors and centrifugal pumps.

Prior art bubble reactor processes typically involve introduction of a single gas phase and a single liquid phase to the reactor. Other variations include the combination of a gas phase plus a solid phase or a three phase process involving a liquid, gas and a solid phase, i.e. a slurry. Such processes are discussed by Y. T. Shah, et al. in *Design Parameters Estimations for Bubble Column Reactors*, American Institute of Chemical Engineers Journal, 28, No. 3, 353 (1982) and S. Lee and Y. Tsui, *Succeed at Gas/Liquid Contacting*, Chemical Engineering Progress, 23 (July 1999). In the present process two liquids, but no gases, are fed to the system. The gas, which is necessary for functioning of the bubble reactor, is generated in situ by the present process. This provides an agitation means for the bubble reactor, preferably the primary means of agitation, thereby decreasing the complexity of the process and increasing overall efficiency. Mass transfer from the gas to the liquid is not a factor that influences the reaction. The gas is a working fluid that controls temperature by its formation and provides agitation by virtue of its buoyancy. Further, the gas formation greatly enhances the kinetic efficiency of the reaction.

The process of the present invention is useful for production of a wide variety of dehydrohalogenated products, for example, 2-methyl-3-chloropropene-1; 2-bromopropene-1; 3-chlorobutene-2; 2,3-dichloro-1-3-butadiene; perfluorobutylethylene; and 4-bromo-3,3,4,4-tetrafluorobutene. It is particularly useful in production of chloroprene from 3,4-dichlorobutene-2.

The process of the present invention enhances the kinetics of the dehydrohalogenation process. That is, it promotes concentration of the catalyst and reactants, due to evaporation of the product, thus resulting in an increase in reaction rate. The process is most effective when the boiling point of the base used is between that of the dehydrohalogenated product and the organic reactant. In instances where an aqueous base is utilized, the boiling point of the base will be that of the aqueous base solution, under the particular reaction conditions. For example, 3,4-dichlorobutene-1 can be dehydrohalogenated to form chloroprene in the presence of 22 wt. % aqueous sodium hydroxide according to the present invention. The boiling point of water in a 22 wt. % aqueous sodium hydroxide solution is 110°–111° C. Under the temperature and pressure conditions of the reaction, the boiling points of chloroprene and 3,4-dichlorobutene-1 are 59° C. and 126° C., respectively. The yield of product under these conditions is greater than 99%.

Reference is now made to FIG. 1 which illustrates a preferred embodiment of the process of the present invention. Reactor 22 is an eight-stage upflow reactor in which dehydrohalogenation of 3,4-dichlorobutene-1 to 2-chloro-1, 3-butadiene (i.e. chloroprene) takes place. The reactor contains 8 perforated metal plates, 26, 28, 30, 32, 34, 36, 38, and 40. Water, 50% sodium hydroxide, phase transfer catalyst, and liquid dichlorobutene reactant are fed through lines 10, 12, 14, and 16, respectively, to line 18 to form a two-phase aqueous/organic liquid stream. It is to be understood that streams 10 and 12 could alternatively be mixed and fed to reactor 8 independently of streams 14 and 16, or all four streams could be fed independently. The stream is fed through line 18 to high shear mixer 42. The high shear mixing causes initiation of the dehydrohalogenation reaction and a rise in temperature. After passing through mixer 42, the stream is fed through line 20 to reactor 22. Dehydrohalogenation of the dichlorobutene continues causing formation of water, chloroprene and sodium chloride. The chloroprene is vaporized along with a portion of the water and is conducted, along with catalyst, sodium hydroxide, sodium chloride and water, up and out through the top of the column. The stream may then be fed via line 44 to steam strippers where chloroprene is removed and by-products are recovered for recycle or disposal. Alternatively, vapor that exits the column overhead, consisting predominantly of chloroprene and water, can be fed to a condenser. The liquid that exists the column overhead, consisting of an organic and aqueous phase, can be conducted to a stripper or other distillation device.

The invention is further illustrated in the embodiments below wherein all parts are by weight.

EXAMPLES

Example 1

An organic liquid composed of 99.5 wt. % 3,4-dichlorobutene-1, and 0.17 wt. % bis (beta hydroxypropyl) cocobenzylamine chloride salt catalyst was fed at a rate of 87 kg/hour to a 0.014 cubic meter metal mixing vessel fitted with a mechanical paddle wheel agitator. An aqueous stream composed of 22 wt. % sodium hydroxide and 78 wt. % water was also fed to the same mixing vessel at a rate of 142 kg/hour. The reactant stream from the mixing vessel was fed continuously to the bottom of a vertical 21 cm diameter, 7.3 m tall metal upflow reactor column having 14 stages. Each stage was separated with perforated metal plates designed to minimize back-flow of liquid. The vaporized dehydrochlorinated product of the reaction, i.e. 2-chloro-1,3-butadiene, and water vapor rose through the column causing agitation and upward entrainment of the immiscible liquid organic and aqueous phases. The heat of reaction maintained the temperature at the bottom of the column at 80° C. and the temperature at the top of the column was 66° C. The pressure at the bottom of the column was 0.17 MPa and the pressure at the top was 0.12 MPa. As the two liquid phases flowed up through the column, liquid vaporized continuously as volatile product formed and pressure continuously dropped. The liquid stream leaving the top of the column was composed of 3 wt. % organic phase and 97 wt. % aqueous phase. Catalyst concentration in the liquid stream leaving the column was 2.9 wt. %. The overhead vapor from the column contained 95 wt. % of organic product and 5 wt. % water vapor. The overhead vapor and liquid streams were fed to a condenser and cooled to 20° C. Analysis of the organic liquid phase from the condenser indicated conversion of the 3,4-dichlorobutene-1 to 2-chloro-1,3 butadiene was 99.7%.

Example 2

An organic liquid composed of 99.5 wt. % 2,3,4-trichlorobutene-1 and 0.13 wt. % bis (beta hydroxypropyl) cocobenzylamine chloride salt catalyst is fed at a rate of 109 kg/hr to a 0.021 cubic meter metal mixing vessel fitted with a mechanical paddle wheel agitator. An aqueous stream composed of 21.7 wt. % sodium hydroxide, 77.5 wt. % water, and 0.8 wt. % sodium chloride is also fed to the same mixing vessel at 179.5 kg/br. The mixed stream from the mixing vessel is fed continuously to the bottom of of a vertical 21 cm diameter, 4.9 m tall, metal upflow reactor column having eight stages. Each stage is separated with a perforated metal plate designed to minimize back-flow of liquid. The vaporized dehydrochlorinated product of the reaction, i.e. 2,3-dichlorobutadiene-1,3, and water vapor rises through the column causing agitation and upward entrainment of the immiscible liquid organic and aqueous phases. The reaction heat maintains the temperature at the bottom of the column at approximately 70° C. and the temperature at the top of the column is approximately 50° C. The pressure at the bottom of the column is approximately 0.06 MPa and the pressure at the top is maintained at approximately 0.025 MPa. As the two liquid phases flow up through the column, liquid is vaporized continuously as volatile product forms and pressure continuously drops. The vapor and liquid from the top of the column are fed to a condenser and cooled to 25° C. The organic liquid phase from the condenser is 2,3-dichlorobutadiene-1,3, which forms in yields in excess of 99%.

Example 3

An organic liquid composed of 99.5 wt. % perfluorobutylethyl iodide and 0.2 wt. % bis (beta hydroxypropyl) cocobenzylamine chloride salt catalyst is fed at a rate of approximately 340 kg/hr to a 0.021 cubic meter mixing vessel fitted with a mechanical paddle wheel agitator. An aqueous stream composed of 22 wt. % sodium hydroxide and 78 wt. % water is fed to the same mixing vessel at approximately 198 kg/hr. The mixed stream from the mixing vessel is fed continuously to the bottom of a vertical 21 cm diameter, 6.1 m tall, metal upflow reactor column having ten stages. Each stage is separated with a perforated metal plate designed to minimize back-flow of liquid. The vaporized dehydroiodinated product of the reaction, i.e perfluorobutylethylene, and water vapor rises through the column causing agitation and upward entrainment of the immiscible liquid organic and aqueous phases. The reaction heat maintains the temperature at the bottom of the column at approximately 75° C. and the temperature at the top of the column at approximately 60° C. The pressure at the top of the column is maintained at ambient pressure. As the two liquid phases flow up through the column, liquid is vaporized continuously as volatile product forms and pressure continuously drops. The vapor and liquid from the top of the column are fed to a condenser and cooled to approximately 25° C. The organic liquid phase from the condenser is perfluorobutylethylene, which forms in excess of 95%.

Example 4

An organic liquid composed of 99.5 wt. % 1,4-dibromo-1,1,2,2-tetrafluorobutane and 0.2 wt. % bis (beta hydroxypropyl)cocobenzylamine chloride salt catalyst is fed at a rate of approximately 262 kg/hr to a mixing vessel fitted with a mechanical paddle wheel agitator. An aqueous stream composed of 22 wt. % sodium hydroxide and 78 wt. % water is fed to the same mixing vessel at approximately 200 kg/hr. The mixed stream from the mixing vessel is fed continuously to the bottom of of a vertical 21 cm diameter, 6.1 m tall, metal upflow reactor column having ten stages. Each stage is separated with a perforated metal plate designed to minimize back-flow of liquid. The vaporized dehydrobrominated product of the reaction, i.e 4-bromo-3,3,4,4-tetrafluorobutene, and water vapor rises through the column causing agitation and upward entrainment of the immiscible liquid organic and aqueous phases. The reaction heat maintains the temperature at the bottom of the column at approximately 75° C. and the temperature at the top of the column approximately 57° C. The pressure at the top of the column is maintained at ambient pressure. As the two liquid phases flow up through the column, liquid is vaporized continuously as volatile product forms and pressure continuously drops. The vapor and liquid from the top of the column are fed to a condenser and cooled to approximately 25° C. The organic liquid phase from the condenser is 4-bromo-1,1,2,2-tetrafluorobutene.

What is claimed is:

1. A process for dehydrohalogenation of a halogenated compound selected from the group consisting of halogenated alkanes and halogenated alkenes, said process comprising A) contacting a first composition comprising said halogenated compound with a second composition comprising a base having a $K_b$ of at least $10^{-9}$, in the liquid phase, in a reactor having multiple stages, at a temperature sufficient to initiate the exothermic reaction of said halogenated compound with said base, thereby forming a dehydrohalogenated compound having a boiling point lower than that of said halogenated compound; and B) maintaining the temperature of the reactor contents at a temperature sufficient to vaporize said dehydrohalogenated compound, thereby causing agitation of said reactor contents and transfer of vaporized dehydrohalogenated compound through said multiple stages of said reactor, said vaporization providing a means of agitation.

2. A process of claim 1 wherein said first composition and said second composition comprise two immiscible liquids.

3. A process of claim 1 wherein said first composition comprises a solution of a halogenated compound in an organic solvent.

4. A process of claim 1 wherein said halogenated compound is a liquid and said base is present as an aqueous solution.

5. A process of claim 1 wherein said halogenated compound is selected from the group consisting of chlorinated alkanes and chlorinated alkenes.

6. A process of claim 1 wherein said halogenated compound is selected from the group consisting of brominated alkanes and brominated alkenes.

7. A process of claim 1 wherein said halogenated compound is selected from the group consisting of iodinated alkanes and iodinated alkenes.

8. A process of claim 1 wherein said halogenated compound is selected from the group consisting of fluorinated alkanes and fluorinated alkenes.

9. A process of claim 1 wherein said reactor is a vertical column.

10. A process of claim 1 wherein the reaction takes place in a series of continuous distinct vessels.

11. A process of claim 1 wherein said base is sodium hydroxide.

12. A process of claim 1 wherein said dehydrohalogenated compound is a chlorinated butadiene.

13. A process of claim 1 wherein said halogenated compound is a chlorinated butene.

14. A process of claim 1 wherein heat is supplied to said reactor to initiate the dehydrohalogenation reaction.

15. A process of claim 1 wherein said first and second compositions are mixed together and then fed to said reactor.

16. A process of claim 15 wherein said first and second compositions are mixed together in a high shear mixing device and then fed to said reactor.

17. A process of claim 1 wherein said second composition additionally comprises a dehydrohalogenation catalyst.

* * * * *